United States Patent [19]

Hyde et al.

[11] Patent Number: 5,910,232

[45] Date of Patent: Jun. 8, 1999

[54] METHOD FOR INHIBITING POLYMER FORMATION IN STYRENE PROCESSING

[75] Inventors: Zara Hyde, Old Bedhampton, United Kingdom; Vincent E. Lewis, Missouri City, Tex.

[73] Assignee: Nalco/Exxon Energy Chemicals, L.P., Sugar Land, Tex.

[21] Appl. No.: 09/095,426

[22] Filed: Jun. 10, 1998

[51] Int. Cl.$^6$ .............................. B01D 3/34; C07C 7/20
[52] U.S. Cl. ................... 203/9; 203/59; 203/98; 203/DIG. 9; 585/4; 585/5; 585/24
[58] Field of Search .............................. 203/8, 9, 59, 98, 203/94, DIG. 9; 585/4, 5, 24

[56] References Cited

U.S. PATENT DOCUMENTS

| | | |
|---|---|---|
| 3,964,978 | 6/1976 | Watson ......................................... 203/9 |
| 4,466,905 | 8/1984 | Butler et al. . |
| 4,670,131 | 6/1987 | Ferrell . |
| 5,254,760 | 10/1993 | Winter et al. . |
| 5,312,952 | 5/1994 | Grossi et al. . |
| 5,396,004 | 3/1995 | Arhancet et al. . |
| 5,648,574 | 7/1997 | Arhancet et al. . |
| 5,733,988 | 3/1998 | Apecetche et al. ........................ 526/74 |
| 5,824,829 | 10/1998 | Maeda et al. ................................ 585/3 |
| 5,844,025 | 12/1998 | Cunkle et al. ............................. 524/99 |

*Primary Examiner*—Virginia Manoharan
*Attorney, Agent, or Firm*—Kelly L. Cummings; Thomas M. Breininger

[57] ABSTRACT

Inhibition performance is improved in styrene processing through the addition of a stable nitroxide free radical compound to the styrene feed and to the reflux of at least one column.

10 Claims, No Drawings

METHOD FOR INHIBITING POLYMER FORMATION IN STYRENE PROCESSING

FIELD OF THE INVENTION

This invention relates generally to styrene antifoulants and, more particularly, to a method for inhibiting polymer formation in styrene processing.

BACKGROUND OF THE INVENTION

Vinyl aromatic monomers, such as styrene, are used extensively for the manufacture of plastics. These monomers undergo undesirable thermal and free radical polymerization during storage, shipping, and particularly during processing. Such polymerization can cause fouling of distillation towers and other equipment used for processing the monomers and can render the monomers unfit for use without further treatment. Accordingly, to minimize polymerization, compounds having polymerization inhibiting activity are commonly injected into the crude styrene-containing feed to the distillation columns. In certain styrene recovery processes, a secondary injection can also be made into the primary column of the distillation section directly above the crude styrene feed to achieve better mixing.

A wide variety of compounds are known in the art and have been employed as polymerization inhibitors. However, while some of these compounds can actually inhibit polymerization (hereinafter referred to as "true inhibitors"), others can merely slow down the polymerization process (hereinafter referred to as "retarders").

True inhibitors completely inhibit polymerization for the period of time during which they are present in the styrene stream. The most frequently utilized true inhibitors are stable nitroxide free radical compounds. U.S. Pat. No. 4,670,131, which is representative of the prior art, discloses the use of stable free radicals, including nitroxides, to inhibit the polymerization of olefinic compounds, such as styrene. Nitroxides are generally recognized as the cornerstone of inhibitor programs because of their superior inhibiting capabilities. Alkyl hydroxylamines have also been utilized in styrene systems, but are not as effective.

Retarders, unlike true inhibitors, do not stop polymerization. Rather, retarders slow down the rate of polymer growth. The compounds commercially employed as retarders are dinitrophenols, such as 2,4-and2,6-dinitrophenol, as well as alkylated homologues such as 2,4-dinitro-o-cresol (DNOC) and 2,4-dinitro-sec-butylphenol. Unfortunately, although dinitrophenols, such as DNOC, are effective retarders, they are extremely toxic. In addition, dinitrophenols have very low solubility, i.e., less than 5%, in both styrene and its precursor ethylbenzene. Companies that use either of these two products typically make up solutions in hot styrene or ethylbenzene to increase solubility. However, the companies are then dealing with a known toxin dissolved in a suspected carcinogen. Although solubility problems can be overcome by using products such as dinitro-sec-butylphenol, the alkyl group does not add any activity to the product. Therefore, while solubility in the hydrocarbons is increased, product activity is decreased.

Furthermore, styrene manufacturers have gone to great lengths to remove air from the product recovery section of their plants. Thus, an inhibitor or a retarder must normally work under anaerobic conditions. The term "anaerobic" is used herein to mean substantially free of oxygen. In other words, although styrene manufacturers attempt to operate air-free processes, trace amounts of oxygen may nonetheless be present. Several known retarders, however, require the presence of oxygen to reduce the amount of polymerization which occurs. For example, U.S. Pat. No. 4,466,905 discloses that phenylenediamines and 2,6-dinitro-p-cresol will inhibit polymerization in the distillation column if oxygen is added.

Both true inhibitors and retarders (such as dinitropenols and phenylenediamines) have been added to the crude styrene feed and added up-stream of the crude styrene feed, e.g., into the styrene-producing reactor effluent and process front end, to inhibit polymer formation. However, because of the overall effectiveness of the true inhibitors, especially the nitroxides, and the undesirable toxicity of most retarders, nitroxides have generally been the preferred polymer inhibitor.

Unfortunately, field application of nitroxides in the distillation section of styrene processes has been slow to develop because of economic and logistical considerations. A need remains to determine whether injecting the nitroxide at particular locations in the styrene process can improve inhibition performance above and beyond what has heretofore been found by directing all of the nitroxide into the crude styrene feed at the beginning of the distillation section.

Accordingly, it would be desirable to provide an improved method for inhibiting polymer formation during aerobic or anaerobic styrene processing using a true inhibitor, particularly a nitroxide. It would also be desirable to determine where in the styrene process the nitroxide could be injected in such a way as to achieve maximal inhibition performance.

SUMMARY OF THE INVENTION

The present invention calls for adding a stable nitroxide free radical compound to the styrene feed and to the reflux of at least one column in a styrene process. The addition of the nitroxide to these locations significantly improves styrene polymer inhibition performance.

DETAILED DESCRIPTION OF THE INVENTION

The present invention is directed to a method for inhibiting polymer formation in styrene processing. In accordance with this invention, a stable nitroxide free radical inhibitor is added to the styrene feed and to the reflux of at least one column in a styrene process. As used herein, the term "styrene feed" means the styrene which is fed into the first column ("crude styrene") and into at least one subsequent column in a distillation section. The term "reflux" is used herein to mean the condensed overheads return line to each column, e.g., the ethylbenzene/styrene monomer (EB/SM) separation column of a styrene process, as well as the benzene-toluene and the light ends and heavy ends purification columns in a styrene process. The term "styrene process" as used herein includes downstream monomer processing, e.g., the production of polystyrene and other polymers. The styrene process may either be aerobic or anaerobic.

The nitroxide free radical inhibitors which may be used in the practice of this invention are described in U.S. Pat. No. 5,254,760, the disclosure of which is incorporated herein by reference. It is believed that other nitroxide free radicals could also be used with desirable results. Suitable nitroxides include: di-tert-butyl nitroxyl, 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6- tetramethylpiperidin-4yl benzoate, 1-oxyl-2,2,6,6-tetramethylpiperidin-4-yl4-tert-butylbenzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl)adipamide, N-(1-oxyl-2,2,6,6-tetramethylpiperidin-4-yl)-caprolactam, N-(1-oxyl-2,2,6,6-tetramethylpiperidin-4-yl)-dodecylsuccinimide, 2,4,6-tris-[N-butyl-N-(1-oxyl-2,2,6,6-tetramethylpiperidin-4-yl]-s-triazine, and 4,4'-ethylenebis(l-oxyl-2,2,6,6-tetramethylpiperazin-3-one).

It is preferred that the total amount of nitroxide which is added to the styrene process be in the range of about 0.5 to about 2000 ppm based on the weight of styrene. More preferably, the total amount of the nitroxide is from about 1 ppm to about 200 ppm, with about 1 ppm to about 50 ppm being most preferred. It is preferred that about 10% to about 90% of the total amount of nitroxide be added to the styrene feed and about 90% to about 10% of the nitroxide be added to the reflux. More preferably, about 20% to about 80% of the total amount of nitroxide is added to the styrene feed and about 80% to about 20% is added to the reflux. Most preferably, about 40% to about 60% of the total amount of nitroxide is added to the styrene feed and about 60% to about 40% is added to the reflux. The nitroxide can be introduced into the styrene feed and the reflux by any conventional method.

A non-toxic retarder, such as phenylenediamine, may also optionally be added to the styrene feed and to the reflux. The phenylenediamine compounds which may be employed in the practice of the present invention are described in U.S. Pat. No. 5,396,004, the disclosure of which is incorporated herein by reference. It is believed that other phenylenediamine compounds could also be used with suitable results.

The present inventors have discovered that the location of the nitroxide addition into the styrene feed and the reflux makes a substantial difference in the performance of the total inhibition program. In the particular case of a styrene process via ethylbenzene dehydrogenation, the use of multiple injection locations, specifically the styrene feed and the reflux from the column where the ethylbenzene/styrene monomer (EB/SM) split is effected, can improve inhibition performance substantially (at least twofold).

EXAMPLE

The following example is intended to be illustrative of the present invention and to teach one of ordinary skill how to make and use the invention. The example is not intended to limit the invention or its protection in any way.

In a styrene recovery configuration in which benzene and toluene (Bz-Tol.) were first separated from crude styrene, a tetramethylpiperidinoxyl type radical was initially injected into the styrene feed to the first and second distillation columns (Bz-Tol. column and EB/SM column, respectively). The treat rates during the evaluation varied, however, the inhibitor readily showed significant efficiency at exceptionally low treat rates, i.e., in the range of 5–10 ppm of nitroxide based on styrene monomer levels.

TABLE 1

| Inhibitor Injection | Trial Day | Polymer Levels (ppm) | |
|---|---|---|---|
| | | EB/SM Column Bottoms | SM Column Bottoms |
| 100% in feed | Pre-trial* | 2000 | 10,000 |
| | 0 | 2100 | 10,100 |
| | 1 | 140 | 2950 |
| | 2 | 115 | 2935 |
| | 3 | 95 | 3250 |
| | 4 | 115 | 3565 |
| 50/50 feed: reflux | 5 | 115 | 2185 |
| | 6 | 130 | 1085 |
| | 7 | 160 | 1300 |
| | 8 | 105 | 950 |
| | 9 | 105 | 850 |
| | 10 | 140 | 1030 |

*Average value in last few days preceding evaluation run.

The data in Table 1 illustrate that switching from the base case retarder chemistry gave a significant polymer reduction in both the EB/SM and SM column bottom streams. Polymer levels in the bottoms of the EB/SM splitter column were reduced by an order of magnitude and further downstream in the styrene monomer finishing column (SM column, polymer levels were reduced by greater than 50%, as shown in Table 1. An analysis of the system and locations where the polymer was being formed suggested that further improvement could be gained by implementing an additional inhibitor injection into the column reflux. When still used in combination with a crude styrene feed injection, this resulted in further drop yielding polymer levels in the final SM column residue that were approximately 35% of the former value. This performance was further fine tuned by optimizing the ratio of the two injections to a final ratio of 40% inhibitor added to the crude SM feed and 60% inhibitor added to the EB/SM column reflux.

While the present invention is described above in connection with preferred or illustratve embodiments, these embodiments are not intended to be exhaustive or limiting of the invention. Rather, the invention is intended to cover all alternatives, modifications and equivalents included within its spirit and scope, as defined by the appended claims.

What is claimed is:

1. A method of inhibiting polymer formation in a styrene process, wherein the process has a styrene feed to a distillation section which includes at least one column and a reflux to said at least one column, comprising the step of adding an effective inhibiting amount of a stable nitroxide free radical compound to the styrene feed and to the reflux of said at least one column, wherein said at least one column is selected from the group consisting of an ethylbenzene/styrene monomer separation column, a benzene-toluene column and light ends and heavy ends purification columns.

2. The method of claim 1 wherein the styrene process is anaerobic.

3. The method of claim 1 wherein the stable nitroxide free radical compound is selected from the group consisting of di-tert-butyl nitroxyl, 1-oxyl-2,2,6,6-tetramethylpiperidine, 1-oxyl-2,2,6,6-tetramethylpiperidin-4-ol, 1-oxyl-2,2,6,6-tetrarmethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4yl benzoate, 1-oxyl-2,2,6,6-tetramethylpiperidin-4-yl 4-tert-butylbenzoate, bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6- tetramethylpiperidin-4-yl) sebacate, bis(1-oxyl-2,2,6,6-tetarnethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1 -oxyl-2,2,6,6-tetramethylpiperidin-4-yl) hexahydroterephthalate, N,N'-bis(1-oxyl-2,2,6,6-tetramethylpiperidin-4-yl)adipamide, N-(1-oxyl-2,2,6,6-tetramethylpiperidin-4-yl)-caprolactam, N-(1-oxyl-2,2,6,6-tetramethylpiperidin-4-yl)-dodecylsuccinimide, 2,4,6-tris-[N-butyl-N-(1-oxyl-2,2,6,6-tetramethylpiperidin-4-yl]-s-triazine, and 4,4'-ethylenebis(1-oxyl-2,2,6,6-tetramethylpiperazin-3-one).

4. The method of claim 1 wherein the nitroxide is added to the process in an amount from about 0.5 ppm to about 2000 ppm based on the weight of the styrene.

5. The method of claim 1 wherein the nitroxide is added to the process in an amount from about 1 ppm to about 200 ppm based on the weight of the styrene.

6. The method of claim 1 wherein the nitroxide is added to the process in an amount from about 1 ppm to about 50 ppm based on the weight of the styrene.

7. The method of claim 1 wherein about 10% to about 90% of the nitroxide is added to the styrene feed and about 90% to about 10% of the nitroxide is added to the reflux.

8. The method of claim 1 wherein about 20% to about 80% of the nitroxide is added to the styrene feed and about 80% to about 20% of the nitroxide is added to the reflux.

9. The method of claim 1 wherein about 40% to about 60% of the nitroxide is added to the styrene feed and about 60% to about 40% of the nitroxide is added to the reflux.

10. The method of claim 1 wherein a phenylenediamine compound is also added to the styrene feed and to the reflux.

* * * * *

UNITED STATES PATENT AND TRADEMARK OFFICE
CERTIFICATE OF CORRECTION

PATENT NO. : 5,910,232
DATED : June 8, 1999
INVENTOR(S) : Zara Hyde and Vincent E. Lewis It is certified that error appears in the above-identified patent and that said Letters Patent is hereby corrected as shown below:

Column 4, Claim 3, Line 60:

tetrarmethylpiperidin-4-one, 1-oxyl-2,2,6,6-

LETTERS PATENT SHOULD READ AS:

tetramethylpiperidin-4-one, 1-oxyl-2,2,6,6-

Signed and Sealed this

Ninth Day of November, 1999

Attest:

Attesting Officer

Q. TODD DICKINSON

Acting Commissioner of Patents and Trademarks